United States Patent [19]
Lam et al.

[11] Patent Number: 4,890,313
[45] Date of Patent: Dec. 26, 1989

[54] BI-DIRECTIONAL X-RAY IMAGER

[75] Inventors: Veronica Y. Lam; Wing-Chee Lam, both of Baltimore, Md.

[73] Assignee: Johns Hopkins University, Baltimore, Md.

[21] Appl. No.: 128,224

[22] Filed: Dec. 3, 1987

[51] Int. Cl.4 .................................... H01J 31/50
[52] U.S. Cl. ................................ 378/189; 378/190; 378/65
[58] Field of Search ............... 378/159, 190, 167, 181, 378/57, 65; 250/458.1

[56] References Cited

U.S. PATENT DOCUMENTS

| | | | |
|---|---|---|---|
| 2,508,449 | 5/1950 | Davis, Jr. et al. | 250/57 |
| 3,434,684 | 3/1969 | Warden | 378/189 |
| 3,560,740 | 2/1971 | Tripp | 378/189 |
| 3,612,867 | 10/1971 | Rabodzel et al. | 250/77 |
| 3,758,723 | 9/1973 | Green et al. | 178/6.8 |
| 4,020,346 | 4/1977 | Dennis | 378/57 |
| 4,052,621 | 10/1977 | Haas | 250/458.1 |
| 4,233,516 | 11/1980 | Trepte | 250/444 |
| 4,239,969 | 12/1980 | Haas et al. | 378/57 |
| 4,297,580 | 10/1987 | Juner et al. | 378/57 |
| 4,365,344 | 12/1982 | Dornheim | 378/189 |
| 4,379,348 | 4/1983 | Haas et al. | 378/57 |
| 4,454,605 | 6/1984 | DeLucia | 378/57 |

Primary Examiner—Carolyn E. Fields
Assistant Examiner—David P. Porta
Attorney, Agent, or Firm—Banner, Birch, McKie & Beckett

[57] ABSTRACT

An x-ray imager system of the type that indicates alignment of patient treatment field with x-ray field, using fluorescence screen and imaging sensor, has a cabinet that permits selection of two pre-determinable orientations of cabinet parts mounting the fluorescence screen and sensor (1) at 90° to each other and (2) in linear alignment with each other, by pivoting of upper and lower portions of the cabinet relative to each other. For this, any axially aligned ring-bearing fixed at 45° to the vertical rotatively joins together respective 45° diagonal ends of the cabinet parts, and a detent holds the diagonal ends in either of the two pre-determinable positions of the cabinet parts to each other. A mirror that relays the image at one orientation can be retracted from position in the light path to avoid the beam, when not used.

8 Claims, 7 Drawing Sheets

BI-DIRECTIONAL X-RAY IMAGER

FIELD OF THE INVENTION

This invention relates generally to therapeutic apparatus and particularly to a system for indicating alignment of X-ray beams with patient areas.

BACKGROUND OF THE INVENTION

Many types of apparatus have been used in locational association with X-ray equipment, including those disclosed in the following U.S. patents:

U.S. Pat. No. 2,508,449 to C. P. Davis, Jr. et al, 5-23-50, shows apparatus that could be pivoted 180° for vertical or for horizontal fluorescopic use;

U.S. Pat. No. 3,612,867 to N. Y. Rabodzei et al, 10-12-71, shows angle-adjustable X-ray/TV apparatus with tiltable reflection element;

U.S. Pat. No. 3,758,723 to D. T. Green et al, 9-11-73, shows an X-ray/TV system with angled mirror;

U.S. Pat. No. 4,233,516 to W. Trepte, 11-11-80, shows fluoroscopic apparatus adjustable to horizontal and vertical positions.

As indicated, the purpose of the imager of the present invention is for taking x-ray images of a patient under treatment to make sure that the treatment region is correctly aligned with the x-ray field. The bi-directional imager was conceived while the present inventor was trying to design an x-ray imager which was to be attached to the rotating gantry of a radiotherapy x-ray machine. To cover the size of the x-ray images, the imager has to have a large fluorescence screen (about 50 by 50 cm) and a mirror of about the same size and these have to be arranged at a precise angle to each other. It is very difficult and very costly to build such an imager which is also retractable.

The retractability is very important. To take an image, the imager has to extend out and position opposite to the x-ray source behind the patient. If the imager does not retract from the extended position, it interferes with the technical setting up of the patient for treatment.

It occured to the inventor that, since a large portion of patient treatments are performed with the therapy machine pointing either in a horizontal position or pointing in vertically downward position, it would be more economical to build an imager that can image these two positions only. In that case, according to the present invention, it need not be attached to or supported by the rotating gantry, rather it can be on a movable cart. However, in order to make the imager bi-directional, the plane of the fluorescence screen with the associated mirror should be able to change direction readily and precisely from vertical to horizontal and vice versa. This is accomplished in this invention.

Among the principal objects and advantages are therefore to provide for the following.

Detection of geometric treatment errors:

Since, as noted, a large portion of patient treatments are performed with the x-ray pointing either vertically or horizontally, a guidance image can be obtained at the same time as the treatment, using principles of this imager. From the obtained position of the anatomic structures, it can be determined whether there is any misalignment of the x-ray field with respect to the target volume. If an error is detected, the patient setup can be adjusted correctly before the full radiation dosage is given.

In case treatment is not performed with the x-ray pointing in either of the two directions, vertically or horizontally, the patient can still be imaged in these two directions as "reference" position with a small dosage of x-rays. The patient can then be treated at other desired angles, but the reference images can be used in collaboration with similar images taken with other diagnostic machines (such as radiotherapy simulators, computed tomography scanners, etc.) which can image the patient in the two "reference" directions as well as in the treatment direction.

Documentation of treatment:

The images obtained by the imager can be recorded on magnetic storage media or optical storage media, and provides a permanent record of how the treatment was carried out.

Versatility in mechanical design:

The imager is relatively compact and easy and quick to position. It has only one imaging arm, but it can be rotated to image the patient with x-rays impinging in a selected one of two different directions (horizontal and vertically downward). It does not require two separate imaging arms, is well supported but lightweight, and convenient to use and can be fabricated at relatively low cost.

Simplicity:

Mechanically, the invention provides one rotating joint connecting two boxes together. The electro-optical components are few and simple to install and service.

In consonance with the above, ramifications of the invention can be said in other ways.

Correct patient setup for radiation therapy treatment relies on the reference anatomic landmarks. This imager can obtain image of such localization landmarks and convert it into electronic signals. By using a video digitizer, the image can be digitized into a computer in real-time. The image can then be enhanced to bring out low contrast objects using digital image processing technique. Thus, it facilitates the comparison of treatment position with the reference position of the patient. From this comparison, any error detected can be corrected before the full dose is delivered.

The video image can be stored in magnetic storage device or optical storage devices for documentation of treatments. It saves storage space compared with the conventional means of using photographic film.

From the brightness of the image and the time of irradiation, the dose delivered to the patient can be calculated. Thus provides an independent method to monitor the dose delivered to the patient.

The system can be extended to cover more angles if (1) in an embodiment the base of the lower box is made into a cylindrical sector and moves on a complementary circular track and (2) in another embodiment the screen can be tilted at a larger angle to the mirror as will be shown.

BRIEF DESCRIPTION OF THE DRAWINGS

The above and other objects and advantages of this invention will become more readily apparent on examination of the following description, including the drawings in which like reference numerals refer to like parts.

FIG. 5a is a view taken at line 5a–5a in FIG. 3a;

FIG. 5b is a view taken at line 5b–5b in FIG. 4a;

FIG. 7 is an elevational diagram on an enlarged scale of a mirror positioner mechanism for use in conjunction with the smaller mirror shown in FIG. 4a;

DETAILED DESCRIPTION

In the Figures, x-rays are indicated by arrows at "X".

Figure 1:
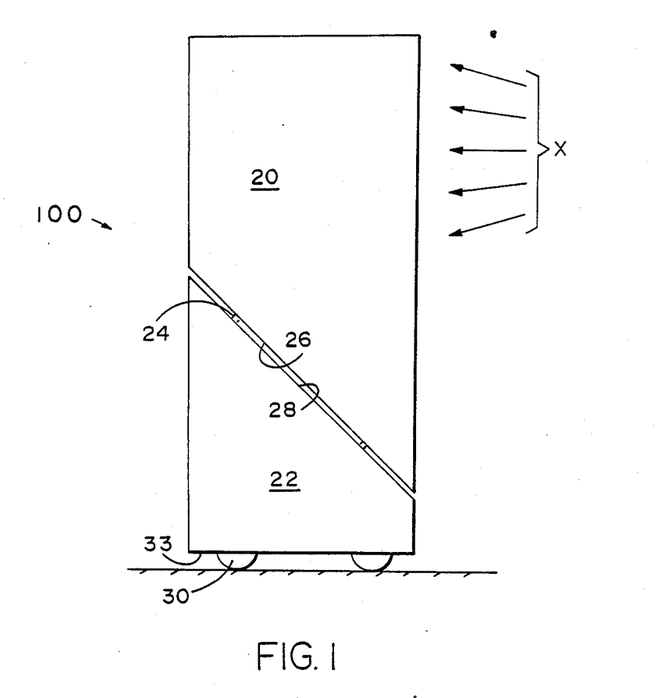
FIG. 1 is an elevational view of the exterior of either a first or a second embodiment of an imager system according to this invention, the appearance being the same, arranged for use observing alignment in horizontal irradiation (arrows) of a patient, not shown.
Figure 2:
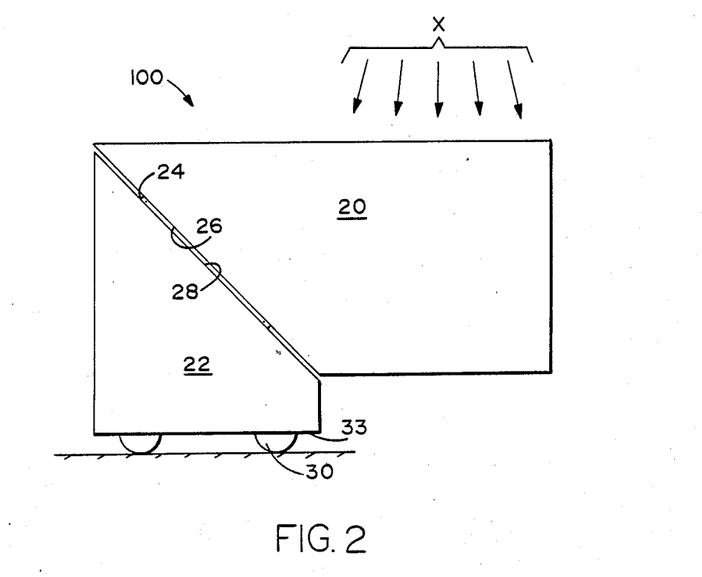
FIG. 2 is an elevational view typical of the first or second embodiment arranged for use observing alignment in vertically downward irradiation of a patient not shown.

FIGS. 1 and 2 show the exterior of the housing means or cabinet of embodiment 100 of the bi-directional x-ray imager according to this invention. The exterior of the embodiment 200 looks the same. The invention includes, depending on embodiment, either three or four electro-optical components, to be described, mounted inside two light-tight boxes 20, 22 connected together by a rotational joint 24, preferably light-tight in itself, and formed at a respective bevel-end of each box. Each of the bevel ends 26, 28 lies at a 45 degree angle to the length of a box 20, 22, as does the rotational joint 24.

The lower box 22 is always vertical, and may have rollers 30 on the lower end thereof.

When the upper box 20 is rotated 180 degrees from the FIG. 1 upper box vertical orientation it assumes the FIG. 2 orientation, horizontally perpendicular to the lower box 22. It may snap precisely into the orientation of either FIG. 1 or FIG. 2, retained by a typical plunger and socket spring detent, described later.

Figure 3A:
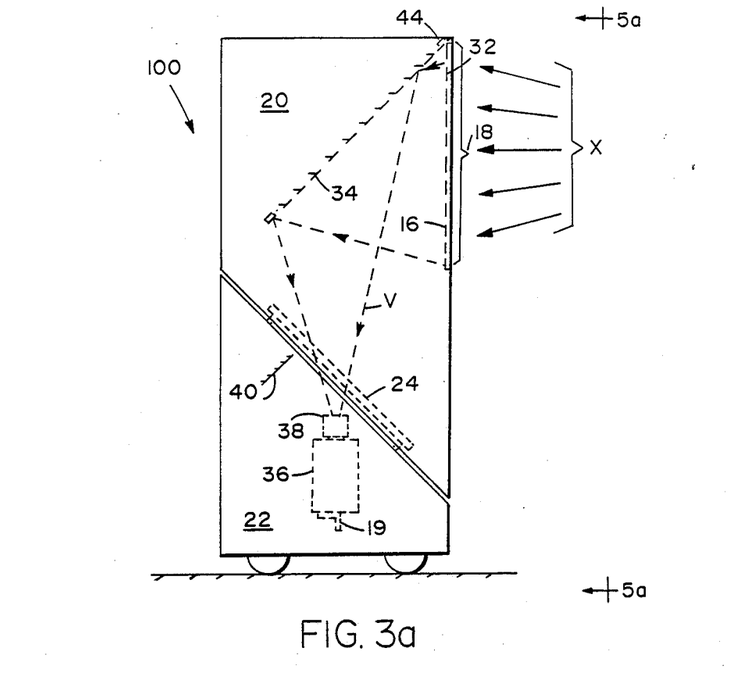
FIG. 3a is an elevational view diagramming in phantom lines the interior of the first embodiment, the preferred embodiment, arranged for use in observing alignment in horizontal irradiation procedures.

Inside the boxes, electro-optical components are arranged to define either of two embodiments, held as by brackets, 19 indicated in FIG. 3a, for example.

Figure 3B:
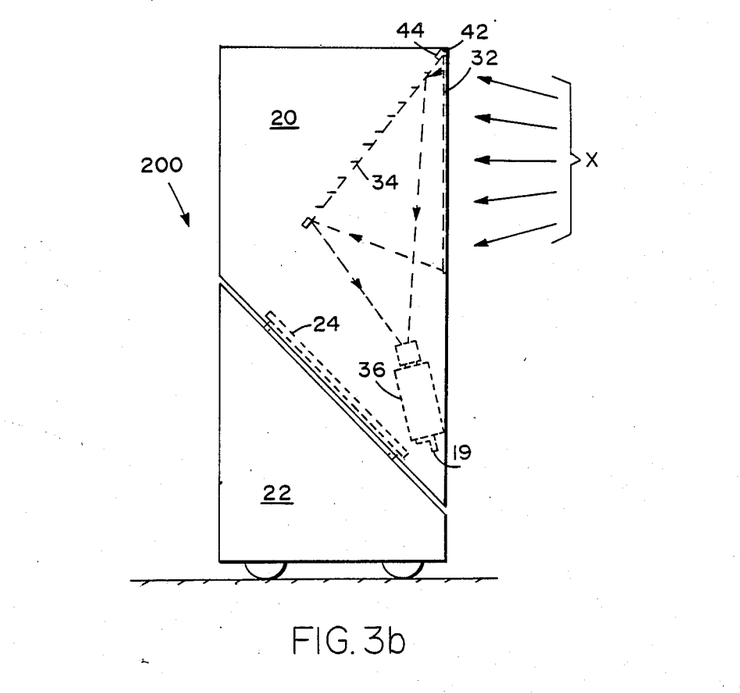
FIG. 3b is a view like that of FIG. 3a but diagramming similarly the interior of the second embodiment arranged for use in observing alignment in horizontal irradiation.
Figure 4A:
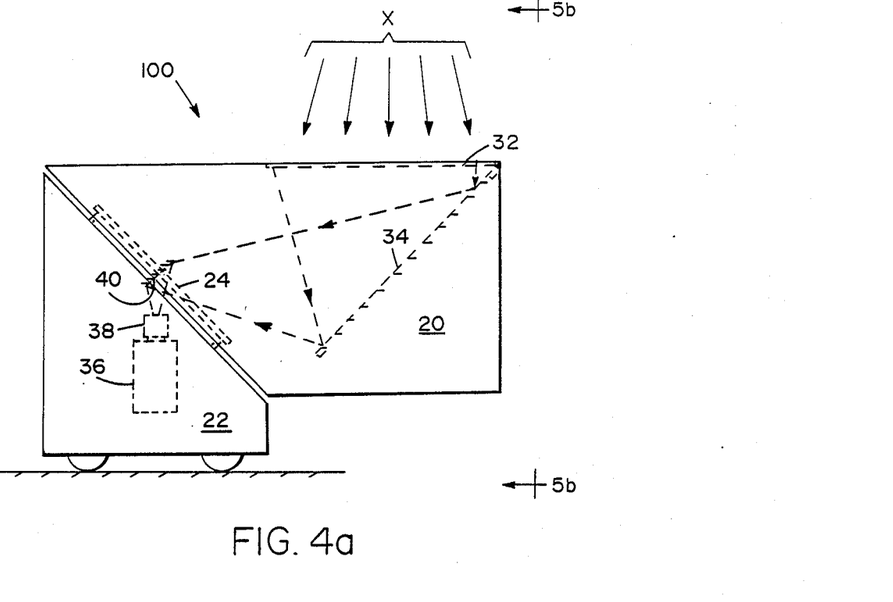
FIG. 4a is an elevational view diagramming the interior of the first embodiment arranged for use observing alignment in vertically downward irradiation procedures.
Figure 4B:
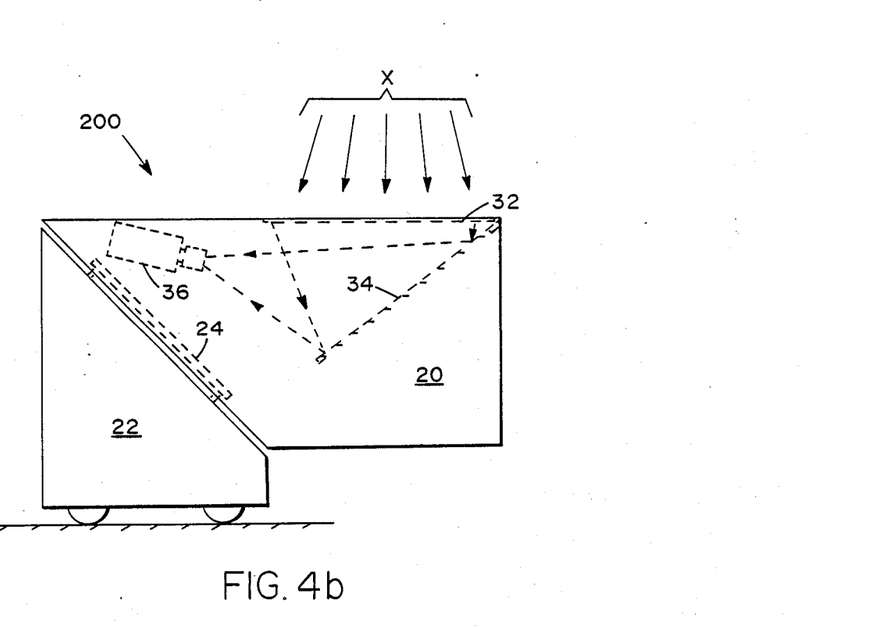
FIG. 4b is like FIG. 4a but shows the interior of the second embodiment arranged for use observing alignment in vertically downward irradiation procedures.

FIGS. 3a and 3b show respectively the two embodiments 100 and 200, with the upper box 20 upright on the lower box 22 in vertical orientation, for monitoring horizontal irradiation (arrows X) and FIGS. 4a and 4b show respectively, the embodiments 100 and 200 with the upper box 20 at 90° to the lower box 22, in horizontal orientation for monitoring vertical irradiation (arrows X).

FIGS. 3a and 4a show that in embodiment 100 of the imager, a fluorescence screen 32 which covers an opening or window 18, covered by a metal plate 16 such as, for example, a 2 mm thick aluminum plate, shown in FIG. 3a but typical of all views of box 20, and first diagonal mirror 34, are mounted in the upper box 20 and a video camera 36 with conventional focussing optics 38 and a second, retractable, diagonal mirror 40 to relay the beam in the second orientation are mounted in the lower box 22. Direction of retraction of mirror 40, out of the field of view "V" of the video camera, may be in the plane of mirror 40, or, as indicated in FIG. 3a, it may be retracted in any other suitable direction. Embodiment 100 provides more room for shielding around the camera to protect it from scattered x-rays than does embodiment 200.

FIGS. 3b and 4b show how in embodiment 200 all the optical and electro-mechanical components: fluorescence screen 32, diagonal mirror 34 and video camera 36, are located in the upper box 20. A second diagonal mirror is unnecessary in embodiment 200 however, there being no relative rotation of components when one box is rotated relative to the other. The amount of space in embodiment 100 for shielding around the video camera 36 is limited, and embodiment 200 is better used in therapy machines that do not generate a large amount of scattered x-rays.

Figure 5A:
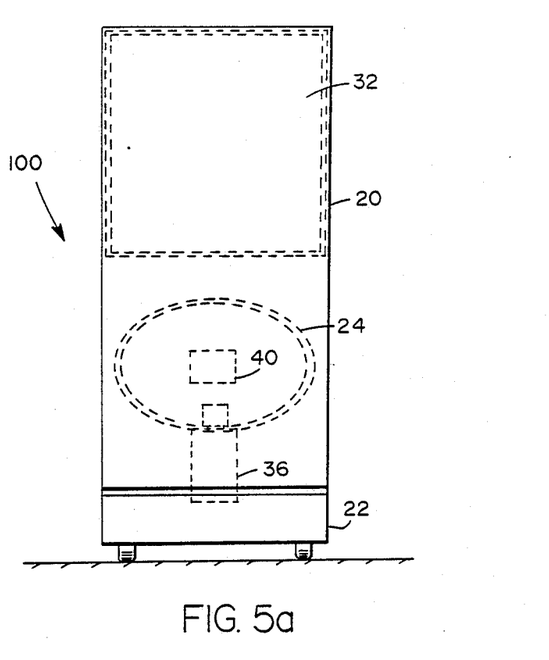

FIG. 5a shows the front view of embodiment 100 with the boxes 20, 22 oriented for receiving horizontal irradiation, rotational joint 24, fluorescence screen 32, video camera 36 and second diagonal mirror 40, which would be retracted in this mode of operation.

Figure 5B:
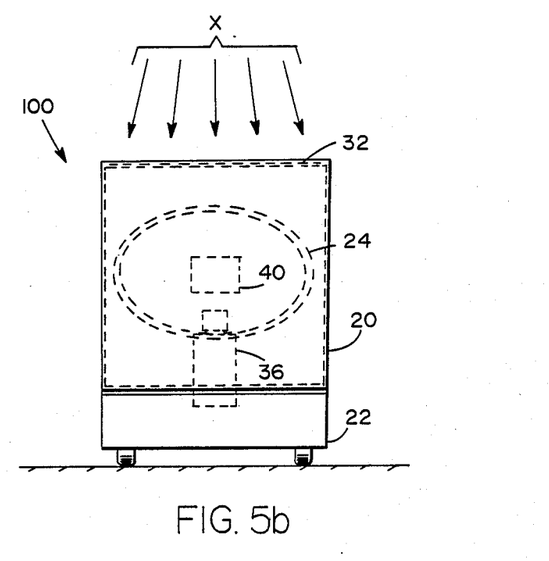

FIG. 5b shows the front view of embodiment 100 with the boxes 20, 22 in orientation for receiving vertical irradiation, rotational joint 24, fluorescence screen 32, video camera 36 and diagonal mirror 40, which in this view would be in the video camera field of view.

Figure 6A:
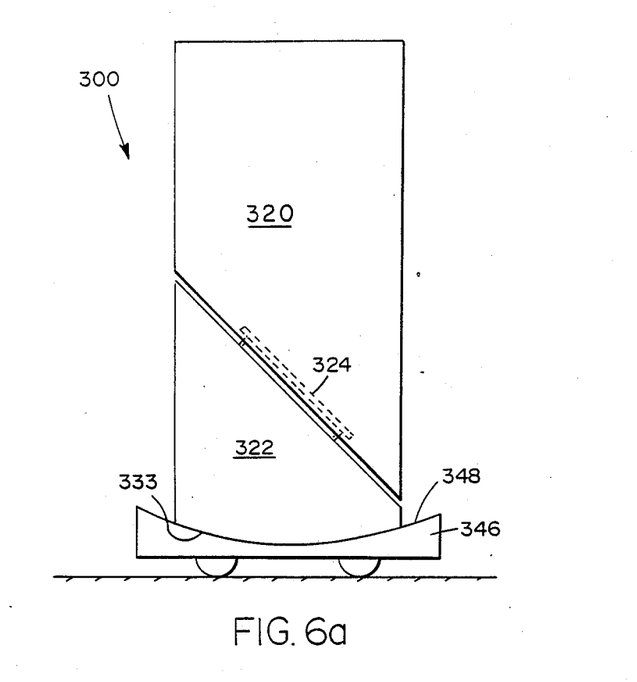
FIG. 6a is an elevational view of a third embodiment.

FIG. 6a shows in embodiment 300 an arrangement permitting angularly adjusting with respect to the vertical an entire imager system represented by the boxes 320, 322 and otherwise similar to either of the embodiments shown above, using a separate base 346 that has a concave upper surface 348 of cylindrical contour with axis horizontal. The bottom 333 of the lower box 322 may have a matching convex contour so that the angular relation of box and base is adjustable at the interface. This provision can supplement but not interfere with the rotary joint 324.

Figure 6B:
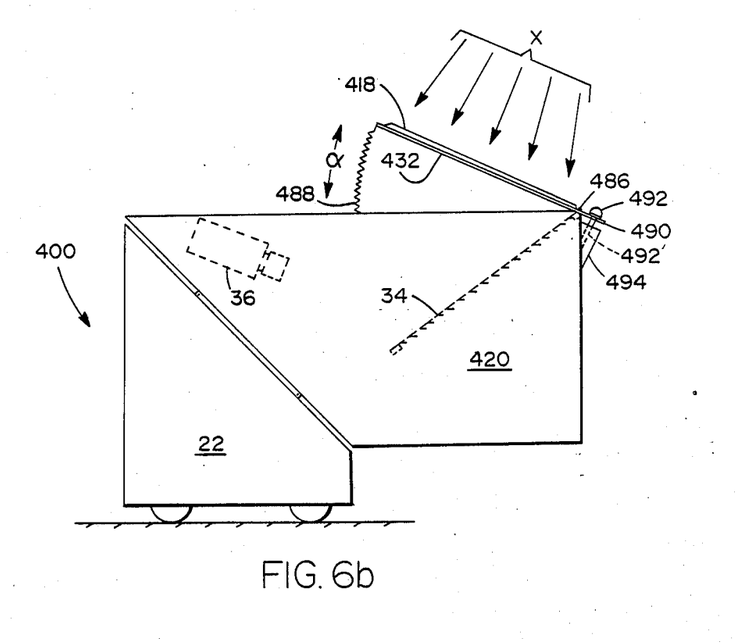
FIG. 6b is an elevational view of a fourth embodiment.

FIG. 6b shows a similar embodiment 400, but with an arrangement that permits the fluorescence screen 432 and window 418 to swing out of the surface of the upper box 420 at one end while the other end is hinged at 486 making an adjustable tilt angle $\alpha$ between the mirror 34 and the fluorescence screen 432 bigger than the normal setting. This allows the fluorescence screen to better receive the x-rays coming from oblique angles. The image obtained by the camera 36 will appear compressed in the tilted direction because the deflected image of the screen is not normal to the camera. However, by using computer image processing technique this distortion can be corrected. A bellows 488 preserves light-tightness. A conventional over-center arm 490 can be adjusted by a screen 492 passing through a slot in the arm and threaded at 492' into a block 494 on the end of the upper box 420.

Figure 7:
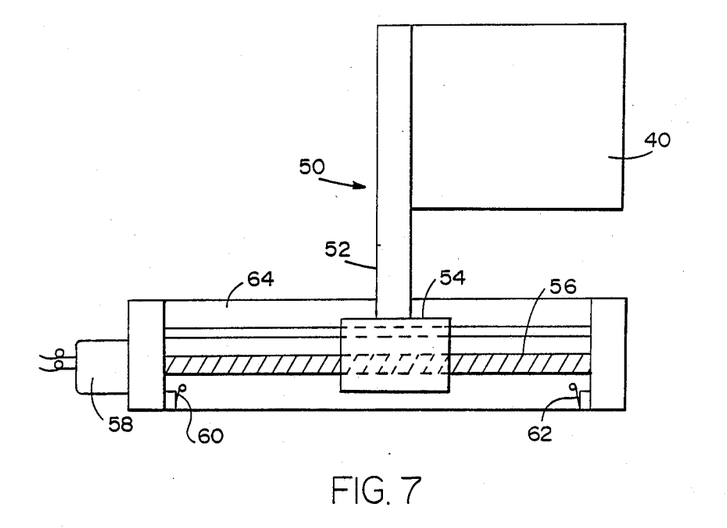

FIG. 7 diagrams a simple positioner 50 for the small mirror 40, FIGS. 3a, 4a, 5a and 5b, in or out of the video camera field of view of the fluorescence screen, as required. The positioner can be mounted on the lower or fixed box (22, central in the field of view in a plane substantially parallel-spaced from the deflection mirror 34, or first diagonal mirror). The mirror may be any ordinary mirror of coated glass at 40 or plastic, or may be thin metal. Supported by a pedestal 52, the small mirror 40 is reciprocated by a nut 54 on a screw 56 rotated by an electric motor 58. Conventional limit switches 60, 62 and an on-off motor reverse switch (not shown) may be provided. The nut may be rectangular and guide on the frame 64. The pedestal 52 may be rotated to change the mode of retraction of the mirror 40, which is fixed at the appropriate horizontal-axis angle to the pedestal.

Figure 8:
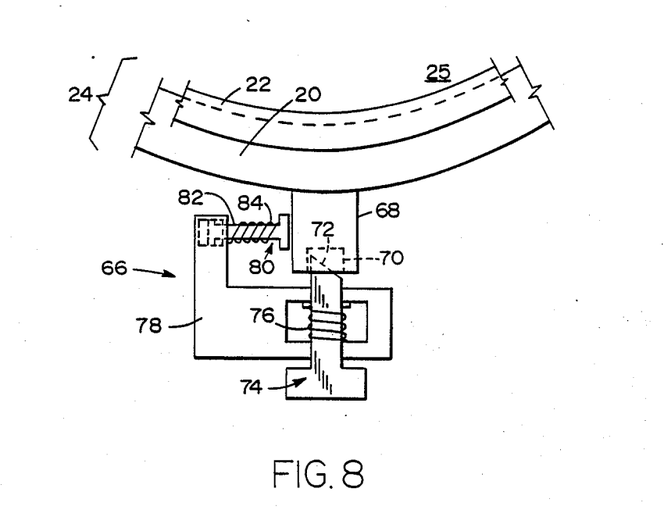
FIG. 8 is a fragmentary axial-view diagram on an enlarged scale of a detent mechanism.

FIG. 8 shows in axial view relative to the rotational joint 24 details of a detent mechanism 66 for fixing the rotational relation of the upper box 20 to that of the lower box 22, fragments of which are shown as comprising parts of the rotational joint 24, at the pre-determined positions 180° apart in rotation.

Preferably two of these are used, respectively on opposite ends of a diameter of the rotational joint 24. A protrusion 68 from one box, (say 20), at the joint has a socket 70 that is engaged by the bevelled end 72 of a square-section plunger 74 slidably held against the inward bias of a spring 76, in frame 78 mounted to the other box (say 22). A buffer 80 comprising a second plunger 82 captured in the frame slidably at right angles to the first plunger 74 has a spring 84 biasing it to extend, and cushions the stopping action of the detent mechanism in rotationally positioning the boxes. Protrusions 68 may be used to actuate the on-off motor reverse switch (not shown but mentioned in the description of FIG. 7) which controls retraction and extension of the small mirror 40.

Figure 9:
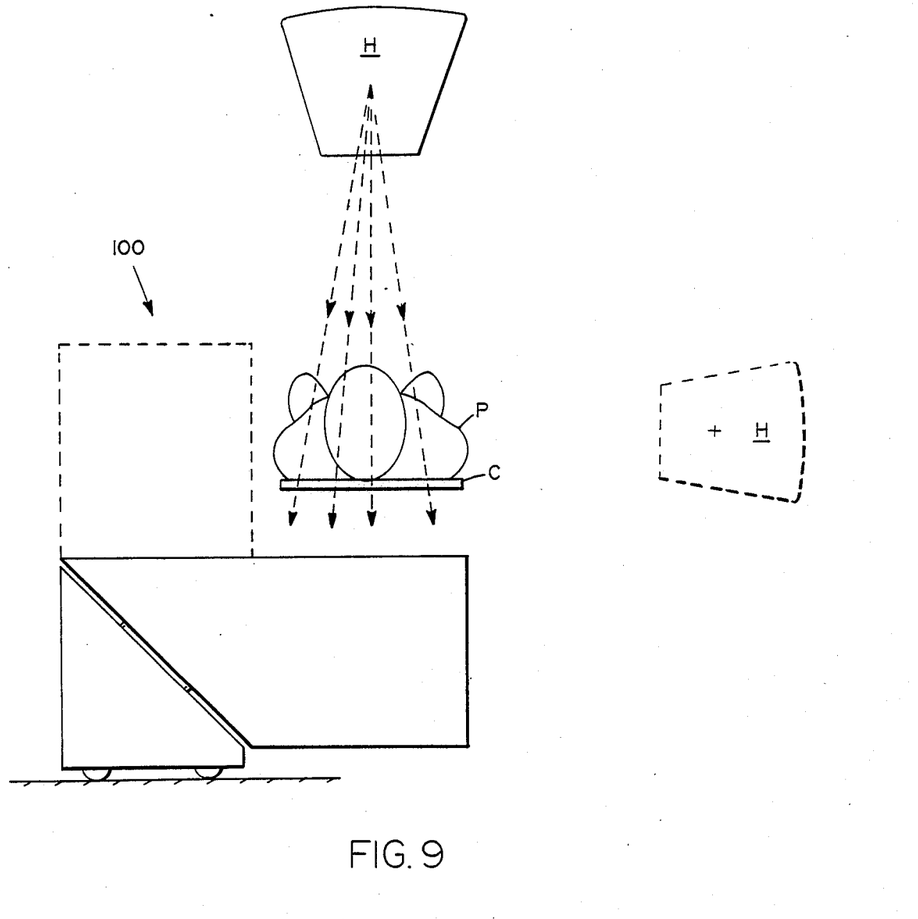
FIG. 9 is an elevational diagram showing an environment of use of apparatus typified by the FIG. 1 and 2 showings, with radiation source and imager shown at two positions (the second position in broken lines) relative to a patient.

FIG. 9 diagrams relations of parts when the system of any embodiment, the first embodiment 100, for example, in use.

A radiation head H may be positioned at either the vertical, or at the horizontal 90° thereto (broken lines) relative to a patient P who is supported on a suitable patient support couch C.

The system of this invention can be easily and quickly oriented by rotating the top box, and rolled into position, to align in correspondence with either position.

Further details of components will be noted from the following description.

The fluorescence screen may be of conventional material such as zinc sulfide, must be large enough to encompass the treatment field of the therapy machine used, and forms a light-tight seal 42 around the window area (area covered by the fluorescence screen) of the upper box.

Preferably, the side of the screen facing the x-ray source may be conventionally covered by a thin aluminum or steel or lead plate (not shown) to provide electronic buildup, making the screen more efficient.

The thin deflection mirror or first diagonal mirror 34 is used as noted to locate the video camera 36 out of the path of the x-rays but in position to receive and record images on the fluorescence screen. In embodiment 100, mirror 34 is set at 45 degrees to the plane of the fluorescence screen 32 and in embodiment 200 is set at about 37.8 degrees to the plane of the fluorescence screen 32 such that the deflected image of the screen is normal to the camera. To prevent scattering of x-rays by the deflection mirror, it is made of a thin (0.10 mm, for example) aluminized sheet of "Mylar" plastic or the like, stretched over a frame indicated at 44 and taped or otherwise conventionally secured to the frame.

The rotation joint 24 may be any conventional, light-tight ring joint (such as a radial ring flange engaged in a "U"-section ring) that will, as indicated, provide a rotational axis between the long axes of the upper and lower boxes 20, 22 at 45 degrees to the long axis (vertical axis) of the lower box 22.

In the embodiment 100 the central region 24 of the ring like joint structure between the boxes may be left open sufficiently not only to provide a thorough optical path from the fluorescence screen to the video camera but also to provide easy access for electrical wiring to the camera. Wiring access can be provided here, also, if needed in the embodiment 200.

Rollers 30 may be of any suitable convenient type, castor or flanged wheels to run on tracks, for example. Lead-shielding against scattered x-rays may be provided around the camera and elsewhere in accordance with conventional practice. The lower box has room inside at the bottom for counterbalancing weights, if desired.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by United States Letters Patent is:

1. A system for use with x-rays including a fluorescence screen excitable to emit light by projection of said x-rays thereon, said protection of x-rays being selectively perpendicular to a first plane and to a second plane perpendicular to the first plane, the improvement comprising:
    orienting means for orienting said fluorescence screen selectively in said first plane and in said second plane for receiving x-rays, said orienting means including first and second boxes, each of said boxes having a forty-five degree joint structure, said joint structures being connected to each other and relatively rotatable through an angle of one hundred and eighty degrees, such that relative rotation of said joint structures through an angle of one hundred and eighty degrees orients said fluorescence screen selectively in the first plane and the second plane.

2. The system of claim 1 further comprising observing means for observing the emission of light, said observing means including a video camera and protecting means for protecting said video camera from x-rays, said protecting means including a diagonal mirror positioned for deflecting the emitted light away from the projection of x-rays and to said video camera.

3. The system of claim 2 wherein said first plane is vertical and said second plane is horizontal.

4. The system of claim 2 further comprising means for further orienting said fluorescence screen including means for pivoting said fluorescence screen to a position outwardly relative to said second box and in alignment with said diagonal mirror, and means for shielding against stray light at said fluorescence screen, including a bellows-like member joining said fluorescence screen and said second box.

5. The system of claim 4 further comprising means for adjustably fixing said fluorescence screen in the position to which it has been pivoted.

6. A system for positioning an x-ray beam-excitable fluorescence screen selectively in a first plane and in a second plane at ninety degrees from the first plane, for axially observing, by a video camera and light directing means for directing light thereonto, at a location out of the x-ray beam, light from the fluorescence screen when excited by x-rays directed onto the fluorescence screen, comprising:

a housing mounting a window opening, the fluorescence screen, the video camera and the light directing means, said housing comprising a first box with a forty-five degree diagonal end structure, a second box with a forty-five degree diagonal end structure, and means joining said first and second boxes for permitting relative rotation of one hundred and eighty degrees therebetween about said diagonal end structures enabling positioning the fluorescence screen selectively in a first plane and in a second plane at ninety degrees from the first plane.

7. A system for receiving through a window thereof at a particular angle a beam from a source of radiation used for patient treatment and indicating radiation-source alignment with the patient, said system having a plurality of components including: a fluorescence screen, a diagonal mirror, means for recording, means for imaging the fluorescence screen on the means for recording, and means for adjusting the beam receiving angle of said system relative to said radiation source, characterized by:

said means for adjusting the beam receiving angle comprising an upper box and a lower box, a first number of components of said plurality of components being mounted in said upper box in position for coacting with said beam, a second number of said plurality of components being mounted in said lower box in position for coacting with said first number of components, said means for adjusting the beam receiving angle further comprising a first rotary joint member at a forty-five degree angle on the bottom of said upper box and a second rotary joint member at a forty-five degree angle on the top of said lower box, fitting said first rotary joint member and rotatable one hundred and eight degrees relative thereto, and said upper and lower boxes and said first and second rotary joint members being light-tight.

8. An imaging system for indicating alignment of radiation relative to a patient undergoing x-ray therapy, using an x-ray source adjustable relative to the patient in angle from horizontal to vertically downward, and including a fluorescence screen positioned for excitation by radiation passed through the patient and impinging on the fluorescence screen, and a video camera positioned for observing said excitation as an indication of said alignment, characterized by:

housing means for adjusting the imaging system for observing said excitation selectively when x-rays are impinging horizontally upon the fluorescence screen and when x-rays are impinging vertically downwardly thereon, said housing means comprising a first box and a second box, each said box having a forty-five degree diagonal end portion, means joining said first box diagonal end portion to said second box diagonal end portion for selective rotation and producing a horizontal relation of said first box with said second box and selectively a relation vertically downward thereon, depending on said rotation.

* * * * *